United States Patent [19]

White

[11] 4,345,086

[45] Aug. 17, 1982

[54] INTERMEDIATE COMPOUNDS IN THE PREPARATION OF SPECTINOMYCIN

[75] Inventor: David R. White, Kalamazoo, Mich.

[73] Assignee: The Upjohn Company, Kalamazoo, Mich.

[21] Appl. No.: 212,943

[22] Filed: Dec. 4, 1980

Related U.S. Application Data

[62] Division of Ser. No. 68,926, Aug. 23, 1979, Pat. No. 4,282,152.

[51] Int. Cl.³ .................. C07D 327/08; C07D 319/24
[52] U.S. Cl. ....................................... 549/16; 549/361
[58] Field of Search ........................ 549/16; 260/340.3

[56] References Cited

U.S. PATENT DOCUMENTS

| | | | |
|---|---|---|---|
| 3,147,277 | 9/1964 | Hoeksema ........................ | 260/340.3 |
| 3,165,533 | 1/1965 | Hoeksema et al. .............. | 260/340.3 |
| 3,642,997 | 2/1972 | Shen et al. ........................... | 424/250 |
| 4,173,647 | 11/1979 | Maier et al. ................... | 260/340.3 X |

FOREIGN PATENT DOCUMENTS 1222508  8/1966  Fed. Rep. of Germany ........ 549/16

OTHER PUBLICATIONS

Rosenbrook et al., Journ. of Antibiotics, vol. 28, pp. 953–964.
Foley et al., J. Org. Chem., 43(22), pp. 4355–4359 (1978).
Rosenbrook et al., Journ. of Antibiotics, vol. 31(5), pp. 451–455 (1978).
Amstutz, Journ. Amer. Chem. Soc. 72, 3420 (1950).

*Primary Examiner*—Ethel G. Love
*Attorney, Agent, or Firm*—Sidney B. Williams, Jr.

[57] ABSTRACT

Process for preparing intermediates of spectinomycin and analogs thereof. Also provides novel intermediates for making spectinomycin and analogs thereof.

1 Claim, No Drawings

INTERMEDIATE COMPOUNDS IN THE PREPARATION OF SPECTINOMYCIN

This is a division, of application Ser. No. 068,926, filed Aug. 23, 1979, now U.S. Pat. No. 4,282,152.

DESCRIPTION

BACKGROUND OF THE INVENTION

1. Field of the Invention

The invention relates to a process for preparing intermediates useful for preparing spectinomycin and analogs thereof. Also includes novel intermediates for making spectinomycin and analogs thereof.

2. Description of the Prior Art

Spectinomycin is a known antibiotic having the formula:

Until recently, spectinomycin has only been prepared by a microbiological process. See Bergy et al., U.S. Pat. No. 3,234,092.

Some analogs of spectinomycin are described by Rosenbrook Jr. et al., in J. Antibiotics, 28, pp. 953 and 960 (1975) and J. Antibiotics, 31, p. 451 (1978). In addition, Carney et al., describes chlorodeoxy derivatives of spectinomycin in J. Antiobiotics, 30, 960 (1977). Further 9-epi-4(R)-dihydrospectinomycin is reported by Foley et al., in J. Org. Chem., 43, 22 pp. 4355–4359 (1978).

However, contrary to the present invention, biological activity is not reported for any of the spectinomycin analogs and derivatives disclosed in the above cited references.

The prior art chemical reactions nearest to those contained in the process of this invention are the reaction of 3,6-di-O-benzoyl-1-bromo-1,4-dideoxy-α-D-glycero-hex-3-enop yranos-2-ulose and methanol to yield 3,6-di-O-benzoyl-1-methoxy-1,4-dideoxy-α-D-glyvero-hex-3-enopyranos-2-ulose and the reactions is disclosed in U.S. application Ser. No. 020,172, filed Mar. 13, 1979 and now abandoned and U.S. application Ser. No. 020,073, filed Mar. 13, 1979.

SUMMARY OF THE INVENTION

The processes of this invention can be used to prepare anomers and asteric mixtures of compounds having the formula:

wherein $R'_1$ through $R'_3$ may be the same or different and are selected from the group consisting of hydrogen, lower alkyl, acyloxyalkyl, lower haloalkyl, lower aminoalkyl, lower alkenyl, lower alkynyl, —OX and —(CH$_2$)n-OX and isomers thereof with the proviso that $R'_1$, $R'_2$ and $R'_3$ are not hydroxy.

X is selected from the group consisting of hydrogen, lower alkyl, lower alkenyl, and lower alkynyl, n is an integer of from one to four;

$R_1$ is hydrogen or lower alkyl;

$R_2$, $R_5$, $R_6$, $R_9$ and $R_{10}$ are selected from the group consisting of hydrogen, lower alkyl, lower alkenyl and lower alkynyl; $R_3$, $R_4$, $R_7$ and $R_8$ are selected from the group consisting of hydrogen, lower alkyl, lower alkenyl, lower alkynyl, and a blocking group consisting of aralkoxycarbonyl, halogenated alkoxycarbonyl and alkoxycarbonyl, with the proviso that one of $R_3$ and $R_4$ is always a blocking group and one of $R_7$ and $R_8$ is always a blocking group; $R'_4$ is aroyl, lower alkyl, or acyl; A is selected from the group consisting of oxygen and sulfur, B and $B_1$ are the same or different and are selected from the group consisting of hydrogen, hydroxy, alkoxy, o-lower alkenyl, thio, thio-lower alkyl and thio-lower alkenyl. Z is halo.

Compounds Ia and Ib can be deprotected to provide spectinomycin-like compounds having anti-bacterial activity. Methods for deprotecting these compounds are described in copending application Ser. No. 020,172, filed Mar. 13, 1979 and now abandoned, and application Ser. No. 020,073, filed Mar. 13, 1979.

Also, methods of using the deprotected compounds are described in said copending applications.

The novel process for preparing the compounds of formula Ia can be represented schematically as follows:

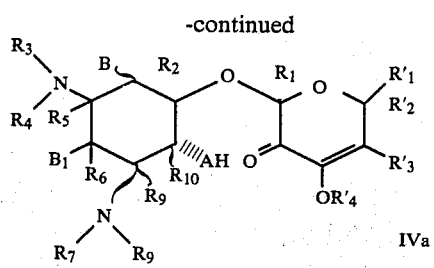

IVa

↓ Silica gel solvent 2a

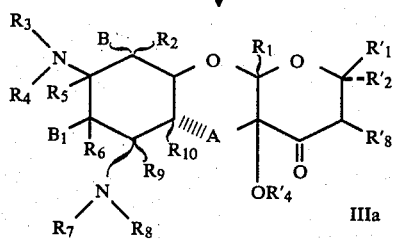

IIIa

↓ Alcoholysis 3a

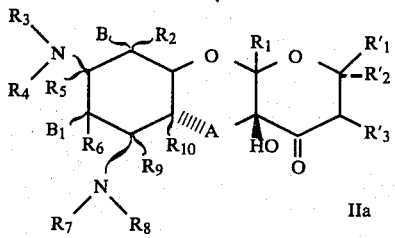

IIa

↓ Hydrolysis 4a

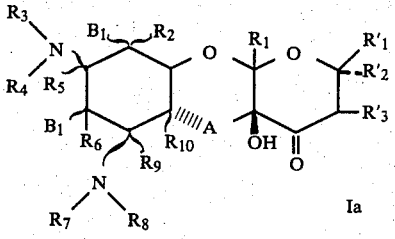

Ia

Compounds of Ia are the same as compounds of Formula IIa except that some of the groups $R'_1$ through $R'_3$ have been deprotected.

The process of this invention for preparing compounds of formula Ib can be represented schematically as follows:

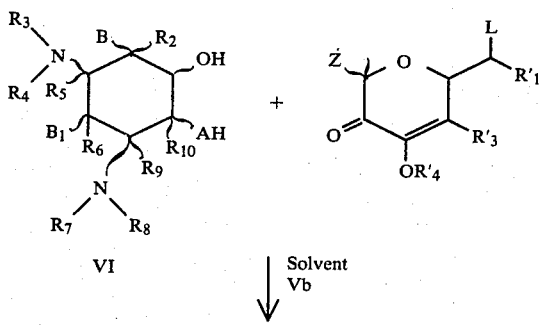

VI

↓ Solvent Vb

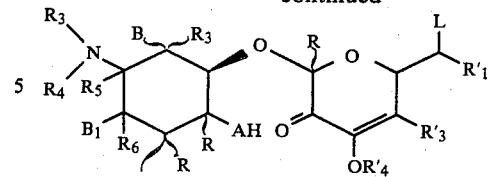

IIIb

↓ Base System 2b

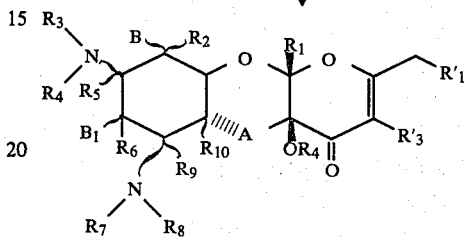

IIb

↓ 3b Hydrolysis

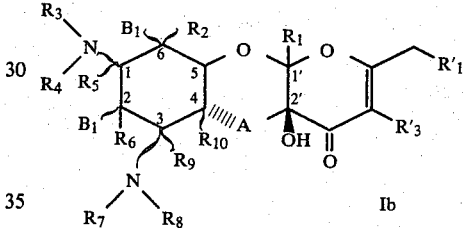

Ib wherein $R'_4$ is acyl and $R_1$ thru $R_{10}$, $R'_1$ thru $R'_3$, A, B, and $B_1$ are the same as above and Z is halo. L is a leaving group such as acyloxy, halo, o-sulfonate, nitro and other groups that can generate unsaturation in the ring by elimination.

The process of this invention provides a novel method for preparing spectinomycin intermediates disclosed in application Ser. No. 020,172, filed Mar. 13, 1979 and now abandoned, and application Ser. No. 020,073, filed Mar. 13, 1979. Specifically, it utilizes a sugar having a 3',4'-olefinic bond.

In the designation of variables herein, the group "—$(CH_2)n$" includes straight chain lower alkyls and isomers thereof.

"Lower alkyl" means methyl, ethyl, propyl, butyl, pentyl, hexyl, heptyl, octyl, and the isomeric forms thereof, "Lower alkenyl" means ethylidene, propylidene, buytlidene, pentylidene, hexylidene, heptylidene, octylidene, and the isomeric forms thereof, "Lower alkynyl" means ethynyl, propynyl, butynyl, pentynyl, hexynyl, heptynyl, octynyl and the isomer forms thereof, "Lower alkoxy" means methoxy, ethoxy, propoxy, butoxy, pentoxy, hexoxy, heptoxy, octoxy and the isomeric forms thereof, "Acyl" means formyl, acetyl, propionyl, butyryl, pentonyl and the isomeric forms thereof, "Aralkyl" means benzyl, phenethyl, phenpropyl, phenbutyl, phenpentyl, diphenylmethyl, diphenyloctyl and isomeric forms thereof and fluorenylmethyl.

"Lower haloalkyl" means -$(CH_2)_n$-halo and isomeric forms thereof. The group contains one to three halo substituents.

"Lower aminoalkyl" means

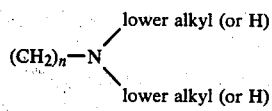

and isomeric forms thereof,

"Aroyl" means benzoyl, substituted benzoyl, napthoyl and substituted napthoyl. The substituted benzoyls and naphthoyls may contain one to three substituents selected from the group consisting of lower alkyl, lower alkoxy, nitro and halo.

"Halogenated alkoxycarbonyl" means mono-, di-, tri-halomethoxycarbonyl; mono-, di-, tri-haloethoxycarbonyl; mono-, tri-halopropoxycarbonyl; mono-, di-, tri-halobutoxycarbonyl, mono-, di-, tri-halopentoxycarbonyl and isomeric forms thereof.

"Halo" means fluoro,, chloro,, bromo and iodo,

"aralkoxycarbonyl" means benzyloxycarbonyl, phenethoxycarbonyl, phenpropoxycarbonyl, phenbutoxycarbonyl, phenpentoxycarbonyl, diphenylmethoxycarbonyl,1 diphenyloctoxycarbonyl and isomeric forms thereof and fluorenylmethoxy carbonyl.

"Alkoxycarbonyl" means isopropyloxy carbonyl, tertiary-butoxy carbonyl, and tertiary-pentyloxy carbonyl.

It is meant that as used in this description and in the appended claims that when more than one hydroxy or alkoxy is present on the sugar moiety herein they may be the same or different.

This invention also pertains to a chemical process for preparing spectinomycin-like compounds.

Thus, the invention process realizes the importance of the stereochemistry at the glycosidic bond, i.e. 1' position of compounds of formula I.

The term "α-anomer" refers to the 1' position of compounds of formula I.

The term "α-anomer" means a 1' substituent below the plane of the ring system an the term "β-anomer" means a 1' substituent above the plane of the ring system. Specifically "β-anomer" means anomers having the C-1' configuration corresponding to spectinomycin.

Actinamines and actinamine derivatives include the aminocyclitols depicted by formula VI.

"Sugars" means substituted pyrans, natural and synthetic sugars, chirals and achirals.

Deprotected compounds which exhibit desirable biological activity are β-anomers of compound I. This glycosidic configuration is found in spectinomycin shown on page 1. Therefore, adequate selectivity at the 1' position is desirable to obtain biologically active analogs of spectinomycin.

Although both α and β anomers may be formed in step 1 of the above process, the β anomers may be preferentially obtained by the separation of β from α anomers following any step in the process. Also the utilization of an available enantiomeric sugar in the initial coupling reaction to give a high proportion of the β anomer, or epimerization of any intermediate or final product may increase the amount of β anomer obtained. Furthermore, asteric mixtures can themselves be utilized an antibacterials in as much as biological activity is present as a consequence of an active anomer therein.

"Anomers and asteric mixtures of a compound" include analogs of spectinomycin within the invention having antibacterial activity. Although the β configuration is the active anomer of the invention, the term "anomers and asteric mixtures" is not meant to be limiting since novel β anomers may also be present without detracting from activity in an asteric mixture. Also α anomers of the spectinomycin analog may in some cases be advantageously anomerized to the active form of the analog. Therefore, the α configuration is not excluded at any step in the invention process.

On the other hand, compounds of use in the invention are products of formula I which have the β configuration because these anomers exhibit antibacterial properties. Separation of the anomers may be accomplished following any step in the process. Preferred β anomers prepared by the process of the invention are compounds including C-2 and C-6 hydroxyls having the following formulae:

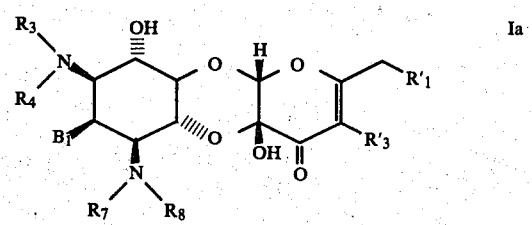

and

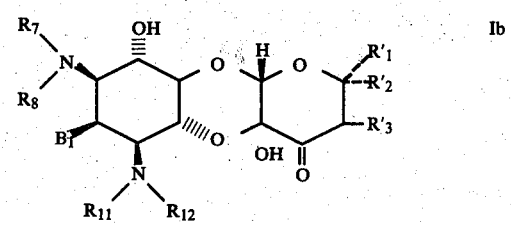

wherein all substitutents are as previously designated.

DETAILED DESCRIPTION OF THE INVENTION

Novel analogs of spectinomycin and intermediates necessary for preparing thereof can be prepared in accordance with the processes outlined above. Process is also a method to prepare spectinomycin. Spectinomycin is an aminocyclitol antibiotic having a unique structure in that it is a single sugar component fused to an actinamine by both a β-glycosidic bond and a hemiketal bond. The method according to the invention for preparation of the analogs having this unique fusion is a synthesis which couples a sugar derivative and a protected actinamine. The sugar may be naturally derived or may be synthetic, chiral or achiral.

More specific examples of the process are as follows:

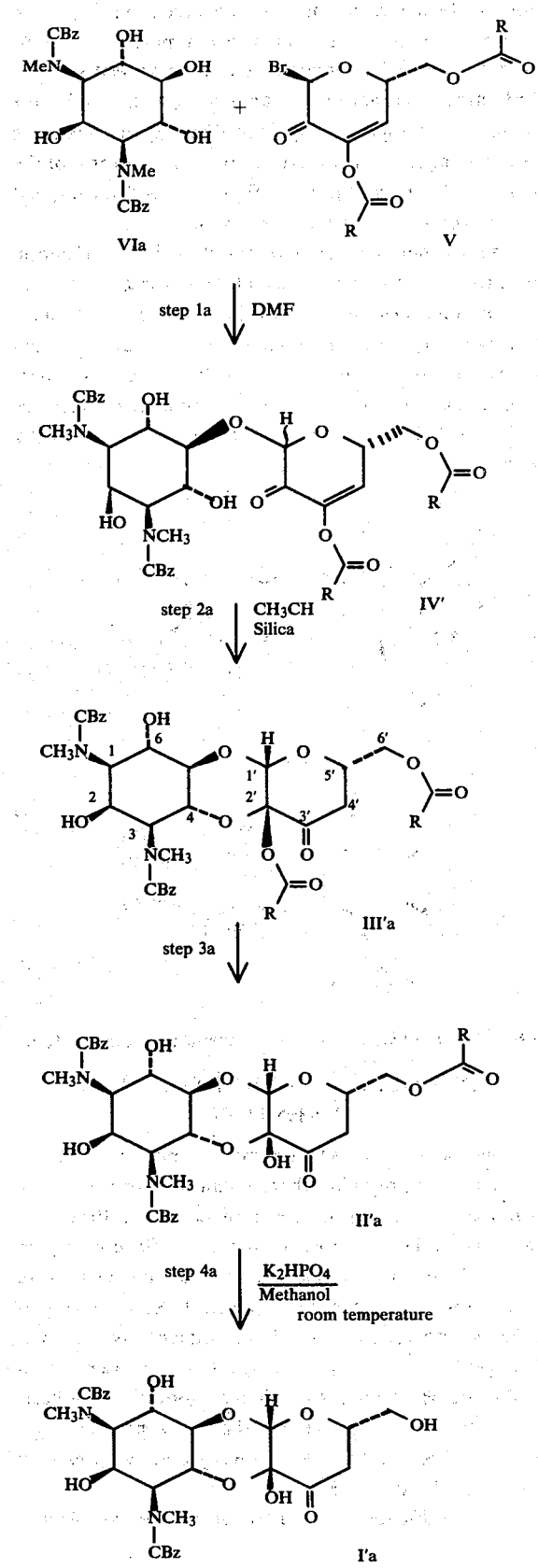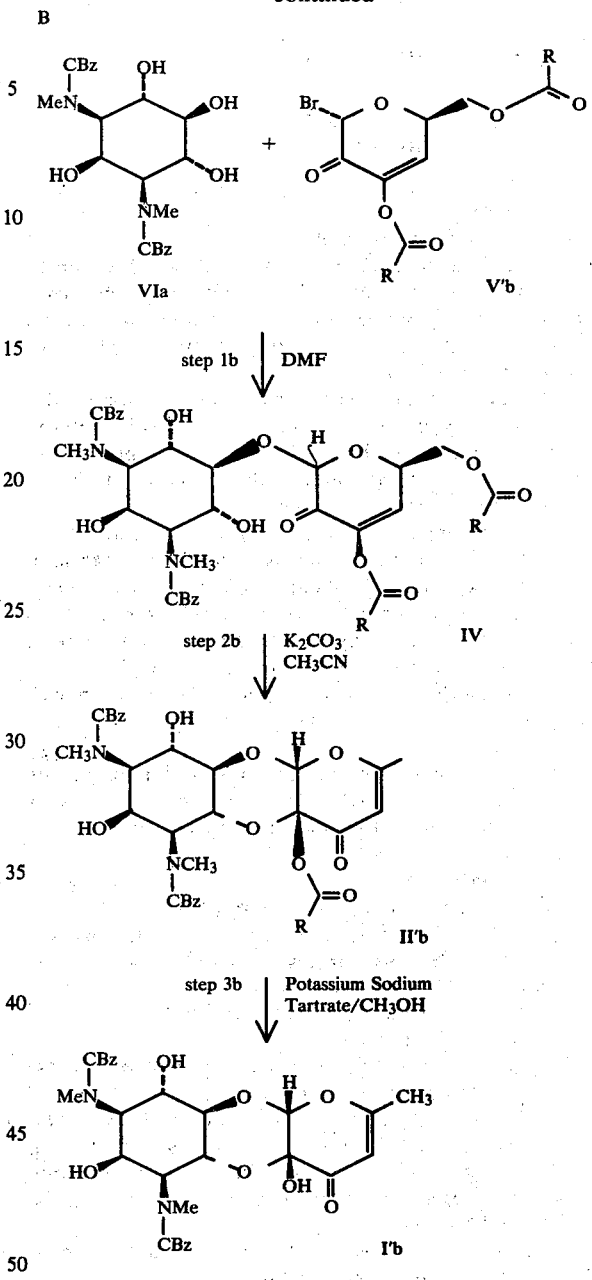

wherein R is lower alkyl of from 1 to 5 carbon atoms, inclusive.

Prior to step 1 the two amino groups of the actinamine derivative VI are protected by blocking each with a blocking group such as aralkoxycarbonyl, haloalkyloxycarbonyl, aryloxycarbonyl or alkoxycarbonyl groups which are well known in the art for this use. For example, background information on the preparation and deprotection of carbobenzyloxy and carbo-tert-butyloxy derivatives of amino acids is described by R. A. Boissonas Chapter, "Selectively Removable Amino Protective Group used in the Synthesis of Peptides., In: Advances in Organic Chemistry, 3:159–190 (1963). Information on the use of the t-butyloxycarbonyl group to block amine is also described in ALDRICH Technical Information Bulletin entitled BOC-OH (September, 1976). Information on the use of trichloroethoxycarbonyl to block amines is disclosed by Windholz et al., Tetrahedron Letters, 2555 (1967). The actinamines can be prepared by methods well known in the art, for example see Suami et al., Bull, Chem. Soc. Jap 43, 1843 (1970).

The sugars are commercially available or can be prepared by methods known in the art; for example such a method is described by Mochalin et al., Chem Het. Comp. 699 (1977) (English translation of KHIM Geterotsiklsoedin, 867 (1977)).

Process A

Step 1a involves a coupling reaction between actinamine VI and sugar V. This step occurs in a solution of N,N-dimethylformamide or similar solvent, such as diethyl ether, tetrahydrofuran or dimethoxy methane sometimes in the presence of a base. The reaction is most efficaciously run under nitrogen atmosphere at ambient temperatures and pressures such as described for a similar reaction by Lichtenthaler et al., Carbohydrate Research p. 363 (1977). The temperature range of the reaction is generally 0° C. to 45° C. with molar ratios of activated sugar in solvent of 0.01 M to 0.5 M added to actinamine in a solution at a concentration of 0.01 M to 0.5 M such that in a reaction mixture the molar ratio of sugar to actinamine ranges from 0.2 to 4. Preferrable reaction conditions are a temperature of 20° C. to 30° C. using dimethylformamide as solvent with the ratio of sugar to actinamine from 3:2 to 2:3. Time of the reaction may range from 4 hours to 1 week but is preferrably from 24 to 48 hours.

The adduct IV produced is generally isolated from the reaction mixture by concentration or from concentration plus vigorous stirring with an excess of water. The resulting solid is taken up in chloroform and subsequently evaporated to dryness to yield the crude intermediate. $\alpha$ and $\beta$ anomers may be further separated into fractions by chromatography on a silica gel column eluted with methanol in chloroform in the ratio of 1:99 to 2:98. However, use of conventional recovery means such as extraction, crystallization, chromatography and combinations thereof are within the process of the invention.

Step 2a may involve hemiketal formation followed by acyl migration and generates a C-3' carbonyl in compound III'a above. The step 2a reaction is conducted by reacting compound IV with silica gel in the presence of a solvent. Initial concentration of adduct in the solvent is from 1 M to 0.001 M, but preferably 0.1 M to 0.001 M. The amount of silica gel is 1 to 5 times the weight of the substitute. The reaction is conducted at a temperature of about 0 to 50, preferably and for a period of time between 1 hour and 7 days, preferably 1 day to 3 days. Solvents that can be used include methanol, ethanol, methylene chloride, toluene and 1-propanol. The preferred solvent is methanol.

In some cases of this invention the hemiketal formation is accompanied by migration of the C-3' substituent on oxygen to the C-2' oxygen with generation of a C-3' carbonyl. This behavior is exemplified in conversion of IV' to III'a and IV' to II'b. In other cases the C-3' substituent on oxygen does not migrate such that a masked or latent C-3' carbonyl is formed; these are enol derivatives. An example is III when $R'_4$ is $CH_3$ or alkoxycarbonyl or aminocarbonyl. The enol ether derivatives can exist as hemiketals or open ketonic isomers or as mixtures of these forms. The deprotection of such enol ethers is described fully in U.S. application Ser. No. 020,073, filed Mar. 13, 1979.

Both of the above cases are novel, useful, selective methods ultimately giving spectinomycin analogs with C-3' carbonyl groups. The masked or latent C-3' carbonyl containing intermediates have unique chemical properties which make them useful for modification by known methods such as halogenation, alkylation, acylation, oxidation and the like. Finally the masked or latent C-3' carbonyl group is much more stable especially to base so that it is part of the more versatile and more easily isolated intermediates.

Compound III'a can be recovered by conventional means such as extraction, crystallization, chromatography and combinations thereof.

In step 3a compound III'a converts to compound II'a by alcoholysis with silica gel as catalyst. Complete conversion occurs in about 4 days.

Step 4a involves deprotection at one or several of the sugar ring positions. Usually these are C-2', C-3' or C-6' and depending on the nature of the protecting group acid and/or base may be used. When base is used as with conversion IIIa to IIa or IIIc to IIc, hydrolysis is conducted at −10° to 50° for a period of 5 minutes to 40 hours. The preferred conditions are 20°-30° for 1 to 20 hours.

Alcohols that can be used include methanol, ethanol and isopropanol, but methanol is preferred. Any base that does not degrade the product can be utilized. This includes sodium bicarbonate, potassium bicarbonate, pyridine, dipotassium hydrogen phosphate, triethylamine, sodium potassium tartrate, but the preferred catalyst is dipotassium hydrogen phosphate. In the first step of a two step process to convert III'a to Ia the C-2' O-acyl group is removed selectively by the above neutral or basic alcoholysis conditions and then the C-6' O-acyl group is removed by basic alcoholysis.

Acid catalysis can also be used to remove the protecting groups of the sugar ring. For example, after the C-6' acyl has been removed from III by using base as described above the remaining C-3' protection may be removed by subsequent acid treatment to give Ia. Alternatively, III may be converted to Ia in one step using acid catalysis.

Acid mediated deprotection is usually done at 0° to 80° preferably at −20°-30° for a period of 1 hour to 3 days, preferably 2 hours to 2 days. Acids used in the art such as hydrochloric, paratoluene sulfuric or phosphoric acids may be used; preferably hydrochloric acid is used. Solvents may include aqueous tetrahydrofuran, aqueous dimethoxyethane, methanol or ethanol. Preferably methanol or aqueous tetrahydrofuran are used.

Process B

Step 1b is conducted in an identical manner as step 1a, however, the sugar used must be L-glucose or an analog thereof.

Step 2b both removes one or two substituents on the sugar moiety of compound IV and generates a C-3' carbonyl. Elimination occurs from C-6' to yield a C-4', C-5' olefin. This step is conducted in the presence of a base system at temperatures from about 0° to 80° C. for a period of from about 2 hours to 1 week. Base systems that can be used includes potassium carbonate, triethylamine, pyridine and alkoxide. A preferred system is potassium carbonate/acetonitrile. One to 20 mole equivalents of base may be used but 1 to 10 is preferred.

The manner in which step 2b is accomplished also depends upon the particular protective groups on the sugar moiety as well as on the actinamine moiety of intermediate IV. In general the protective groups on the sugar moiety are less difficult to remove than those on the actinamine moiety. Step 2b is a process for mild and selective generation of the important C-3' carbonyl by elimination.

The C-6' derivative which may undergo elimination is described in U.S. Ser. No. 020,073, filed Mar. 13, 1979. For example, acetates eliminate acetic acid, benzoate, benzoic acid, benzyl ethers eliminate benzyl alcohol, haides eliminate hydrogen halide. These are non-limiting examples of elimination occuring in step 2b.

The intermediates of this invention, especially the products of step 2b are useful materials for synthesis of a variety of analogs. This is done by changing functional groups of the intermediates by known methods such as halogenation, reduction, oxidation, chain extension and the like.

The compound of formula Ib is removed from the reaction mixture by conventional methods such as precipitation, crystallization or concentration followed by chromatography.

Compounds Ia and Ib can be converted to active spectinomycin analogs by deblocking the actinamine moieties thereof. The particular condition of the blocking depends upon the particular group, i.e. group $R_3$ or $R_4$ and $R_7$ or $R_8$ that block the amine on the actinamine ring. Also by suitable choice of $R_3$, $R_4$, $R_7$ and $R_8$ and by suitable choice of deprotecting conditions known in the art, a C-4', C-5' olefin may remain intact or may be reduced during deprotection. Where that group is benzyloxy carbonyl or aralkoxy carbonyl the deprotection can be conducted under from $-10$ psi to $+200$ psi of hydrogen over a conventional catalyst such as palladium black, palladium on carbon, palladium on barium sulfate, or palladium on barium carbonate, which is suspended in a solvent, for example isopropanol, absolute ethanol, ethyl acetate, toluene or tetrahydrofuran.

Alternatively, deblocking of compounds wherein $R_3$ or $R_4$ and $R_7$ or $R_8$ are alkoxycarbonyl or aryloxycarbonyl can be conducted in the presence of an acid in solvent such as nitromethane and methylene chloride.

When $R_3$ or $R_4$ and $R_7$ or $R_8$ are haloalkoxycarbonyl, the deblocking is preferably conducted in the presence of zinc.

Each step of the above processes can be conducted on asteric mixtures of various anomers or on the desired $\beta$ anomer itself obtained by resolution or separation at any stage in the process. The remaining steps may be conducted on $\beta$-intermediates resulting in the desired biologically active anomers.

The preferred method is to separate $\beta$ anomers from the mixture resulting from step 1 coupling of sugar and actinamine and to conduct subsequent steps of the process on the $\beta$ anomers producing only analogs of spectinomycin which are biologically active.

Separation of the anomers from asteric mixtures can be accomplished with modification obvious to those skilled in the art utilizing conventional methods of resolution. For example, compound IV may be separated so as to obtain a desired $\beta$ component by chromatography on a silica gel column eluted with a mixture of methanol in chloroform in the ratio of 1:99 to 2:98. Likewise, separation of $\beta$ anomers may be effected on an asteric mixture of compound V by pooling $\beta$ fractions obtained on a silica gel chromatograph with a chloroform methanol eluent. Subsequent evaporation to dryness in vacuo yields a separated hemiketal having the $\beta$ structure.

The following described examples of intermediates useful in the preparation of spectinomycin and anologs thereof are indicative of the scope of this invention and are not to be construed as limitative. Those skilled in the art will promptly recognize variations from the procedure described as well as reaction conditions and techniques of the invention process.

For example, for each of the preparations and examples in the following description, corresponding steroisomers for each named compound is contemplated to be within the scope of the invention.

EXAMPLE 1

Anomeric mixture of
N,N'-dicarbobenzyloxy-5-O-[3'6,'-di-O-acetyl-4'-deoxy-α-D-glycero-hex-3'-enopyranos-2'-ulosyl]actinamine and
N,N-dicarbobenzyloxy-5-O-[3',6'-di-O-acetyl-4'-deoxy-β-D-glycero-hex-3'-enopyranos-2'-ulosyl]actinamine To a solution of 3,6-di-O-acetyl-1-bromo-1,4-dideoxy-α-D-glyero-hex-3-enopyranos-2-ulose (0.61 g, 2 mmole) in 10 ml of dimethylformamide is added 0.95 g (2 mmole) of N,N-biscarbobenzyloxy actinamine The reaction mixture is stirred at room temperature under nitrogen atmosphere. After 49.5 hours the solution is poured into ice water with stirring. The solid precipitate is filtered and washed with water. The resulting material is chromatographed on silica gel utilizing 1:9 acetone/chloroform to yield an anomeric mixture of N,N'-dicarbobenzyloxy-5-O-[3',6'-di-O-acetyl-4'-deoxy-α-D-glycero-hex-3'-enopyranos-2'-ulosyl]actinamine and N,N'-dicarbobenzyloxy-5-O-[3',6'-di-O-acetyl-4'-deoxy-β-D-glycero-hex-3'-enopyranos-2'-utosyl]actinamine.

EXAMPLE 2

Anomeric mixture of
N,N'-dicarbobenzyloxy-5-O-[3',6'-di-O-acetyl-4'-deoxy-α-L-glycero-hex-3'-enopyranos-2'-ulosyl]actinamine and
N,N-dicarbobenzyloxy-5-O-[3',6'-di-O-acetyl-4'-deoxy-β-L-glyero-hex-3'-enopyranos-2'-ulosyl]actinamine To a solution of 3,6-di-O-acetyl-1-bromo-1,4-dideoxy-β-L-glycero-hex-3-enopyranos-2-ulose (0.61 g, 2 mmole) in 10 ml of dimethylformamide is added 0.95 (2 mmole) of N,N'-biscarbobenzyloxyactinamine. The reaction The reaction mixture is stirred at room temperature under a a nitrogen atmosphere. After 49.5 hours the solution is poured into water with stirring. The solid precipitate is filtered and washed with water. The resulting material is chromatographed on silica gel utilizing 1:9 acetone/chloroform to yield an anomeric mixture of mixture of N,N'-dicarbobenzyloxy-5-O-[3',6'-di-O-acetyl-4'-deoxy-α-L-glycero-hex-3'-enopyranos-2'-ulosyl]actinamine and N,N-dicarbobenzyloxy-5-O-[3',6'-di-O-acetyl-4'-deoxy-β-L-glycero-hex-3'-enopyranos-2'-ulosyl]actinamine

EXAMPLE 3

Anomeric mixture of
N,N'-dicarbobenzyloxy-5-O-[3',6'-di-O-benzoyl-4'-deoxy-α-L-glycero-hex-3'-enopyranos-2'-ulosyl]actinamine and
N,N'-dicarbobenzyloxy-5-O-[3',6'-di-O-benzoyl-4'-deoxy-β-L-glycero-hex-3'-enopyranos-2'-ulosyl]actinamine 3,6-Di-O-benzoyl-1-bromo-1,4-dideoxy-α-L-glycero-hex-3-enopyranos-2-ulose (0.86 g, 2 mmole) and N,N- biscarbobenzyloxy actinamine (0.95 g, 2 mmole) are dissolved in dimethylformamide (10.0 ml) and allowed to stir at room temperature. After 49.5 hours the solution is poured into ice water (50 ml) with stirring. The solid precipitate is filtered and washed with water. The material is taken up in 1:9 acetone/chloroform and chromagraphed on silica gel (100 ml), 30 ml fractions being taken. The major product anomeric mixture of N,N'-dicarbobenzyloxy-5-O-[3',6'-di-O-benzoyl-4'-deoxy-α-L-glycero-hex-3'-enopyranos-2'-ulosyl]actinamine and N,N'-dicarbobenzylosy-5-O-[3',6' di-O-benzoyl-4'-deoxy-β-L-glycero-hex-3'-enopyranos-2'-ulosyl]actinamine is obtained from combined fractions having a TLC component at $R_f=0.25$ in 1:9 acetone/chloroform. The combined fractions are essentially homogeneous as judged by TLC and weigh 0.38 g (23%).

$UV_{EtOH}$ 230 ($\epsilon=27,350$); MS(trisilyl): 1040 (M+), 1025 (M-15), 905 (M-CO$_2$CH$_2$C$_6$H$_5$)

CMR (CD$_3$COCD$_3$): Characteristic peaks at 57.5 and 60.5 (C-1 and C-3), 74.5 (br. doublet C-2), 88.5 and 89.8 (singlets, C-2' of two closed forms), 99.5 (doublets), 119 (doublets, C-4' of open forms), 128–138 (aromatic carcons), 142.2 and 143.7 (singlets, C-3'), 137.3 (singlet, urethane carbonyls), 166.7 (benzoate carbenzyls), 183.5 (singlet, C-2' open form). The CRM is consistent with an anomeric mixture containing open and several closed forms when compared to a reference standard. PMR shows the required signals for all protecting groups.

EXAMPLE 4

Anomeric mixture of
N,N'-dicarbobenzyloxy-5-O-[3',6'-Di-O-benzoyl-4'-deoxy-α-D-glycero-hex-3'-enopyranos-2'-ulosyl]actinamine and
N,N'-dicarbobenzyloxy-5-O-]3',6'-di-O-benzoyl-4'-deoxy-β-L-glycero-hex-3'-enopyranos-2'-ulosyl]actinamine 3,6-Di-O-benzoyl-1-bromo-1,4-dideoxy-α-D-glycero-hex-3-enopyranos-2-ulose (0.86 g, 2 mmole) and N,N-biscarbobenzyloxy actinamine (0.95 g, 2 mmole) are dissolved in dimethylformamide (10.0 ml) and allowed to stir at room temperature. After 49.5 hours the solution is poured into ice water (50 ml) with stirring. The solid precipitate is filtered and washed with water. The material is taken up in 1:9 acetone/chloroform and chromatographed on silica gel (100 ml), 30 ml fractions being taken. The major product is obtained from combined fractions having a TLC component at $R_f=0.25$ in 1:9 acetone/chloroform. The combined fractions are essentially homogeneous as judged by TLC and weigh 0.38 g (23%).

$UV_{EtOH}$ 230 ($\epsilon=27,350$); MS(trisilyl): 1040 (M+), 1025 (M-15), 905 (M-CO$_2$CH$_2$C$_6$H$_5$)

CMR (CD$_3$COCD$_3$): Characteristic peaks at 57.5 and 60.5 (C-1 and C-3), 74.5 (br. doublet C-2), 88.5 and 89.8 (singlets, C-2' of two closed forms), 99.5 (doublets), 119 (doublets, C-4' of open form), 128–139 (aromatic carbons), 142.2 and 143.7 (singlets, C-3'), 137.3 (singlet, urethane carbonyls), 166.7 (benzoate carbonyls), 183.5 (singlet, C-2' open form). The CRM is consistent with an anomeric mixture containing with open and several closed forms as compared to a reference standard. PRM shows the required signals for all protecting groups.

Utilizing the procedure of Examples 1, 2, 3 and 4 but substituting the appropriate sugars for the sugars used in those examples are obtained in the adducts of Tables I and II.

TABLE I

| B | B$_1$ | R'$_1$ | R'$_2$ | R'$_3$ | R'$_4$ |
|---|---|---|---|---|---|
| OH | OH | H | CH$_2$OCOCH$_5$ | H | CH$_3$ |
| OH | OH | H | CH$_2$OCOC$_6$H$_5$ | H | COC$_6$H$_5$ |
| OH | OH | H | CH$_2$OCOCH$_3$ | H | C$_2$H$_5$ |
| OH | OH | CH$_3$ | CH$_3$ | H | CH$_3$ |
| OH | OH | H | CH$_3$ | H | CH$_3$ |
| OH | OH | H | C$_2$H$_5$ | H | CH$_3$ |
| OH | OH | C$_2$H$_5$ | C$_2$H$_5$ | H | CH$_3$ |
| OH | OH | CH$_3$ | CH$_3$ | H | COC$_2$H$_5$ |
| OH | OH | H | CH$_3$ | H | COCaH$_5$ |
| OH | OH | H | C$_2$H$_5$ | H | COCaH$_5$ |
| OH | OH | C$_2$H$_5$ | C$_2$H$_5$ | H | COCaH$_5$ |
| 5H | 5H | H | C$_2$OCOCH$_3$ | H | CH$_3$ |
| 5H | OH | H | CH$_2$OCOCH$_3$ | CH$_3$ | CH$_3$ |

TABLE II

| B | B$_1$ | R'$_1$ | R'$_2$ | R'$_3$ | R'$_4$ |
|---|---|---|---|---|---|
| OH | OH | H | CH$_2$OCOCH$_5$ | H | CH$_3$ |
| OH | OH | H | CH$_2$OCOC$_6$H$_5$ | H | COC$_6$H$_5$ |
| OH | OH | H | CH$_2$OCOCH$_3$ | H | C$_2$H$_5$ |
| OH | OH | CH$_3$ | CH$_3$ | H | CH$_3$ |
| OH | OH | H | CH$_3$ | H | CH$_3$ |
| OH | OH | H | C$_2$H$_5$ | H | CH$_3$ |
| OH | OH | C$_2$H$_5$ | C$_2$H$_5$ | H | CH$_3$ |
| OH | OH | CH$_3$ | CH$_3$ | H | COC$_2$H$_5$ |
| OH | OH | H | CH$_3$ | H | COCaH$_5$ |
| OH | OH | H | C$_2$H$_5$ | H | COCaH$_5$ |
| OH | OH | C$_2$H$_5$ | C$_2$H$_5$ | H | COCaH$_5$ |
| 5H | 5H | H | C$_2$OCOCH$_3$ | H | CH$_3$ |
| 5H | OH | H | CH$_2$OCOCH$_3$ | CH$_3$ | CH$_3$ |

EXAMPLE 5

Reaction of the anomeric mixture prepared in Example 1

An anomeric mixture of N,N'-dicarbobenzyloxy-5-O-[3',6'-di-O-acetyl-4'-deoxy-α-D-glycero-hex-3'-enopyranos-2'-ulosyl]actinamine and N,N'-dicarbobenzyloxy-5-O-[3',6'-di-O-acetyl-4'-deoxy-β-D-glycero-hex-3'-enopyranos-2'-ulosyl]actinamine (8.58 g) is dissolved in 160 ml of methanol and stirred with 50 g of silica gel for two days. Celite (200 ml) is added to the stirred mixture and the slurry is filtered and washed with methanol (4×100 ml). The filtrate is concentrated and taken up in 4% acetone in chloroform and placed in 1 liter of wet packed silica gel. After using 2 liters, the solvent is changed to 6% acetone (2 liters), then 10% acetone, 50 ml fractions are taken. Upon combining like fractions three products are obtained:

(a) N,N'-dicarbobenzyloxy-2'-O-acetyl-6'-acetoxy 1'-epi-2'-epi-spectinomycin,
(b) N,N'-dicarbobenzyloxy-2'-O-acetyl-6'-acetoxy-spectinomycin and
(c) N',N'-dicarbobenzyloxy-6'-acetoxyspectinomycin.

It is found that upon standing in methanol plus silica gel, compound b is converted to compound c.

Utilizing procedures similar to that utilized in Example 5 but substituting other anomeric mixtures of adducts for anomeric mixtures utilized therein the compounds of Tables III and IV are obtained:

TABLE III

| B | B$_1$ | R'$_1$ | R'$_2$ | R'$_3$ | R'$_4$ |
|---|---|---|---|---|---|
| OH | OH | CH$_3$ | CH$_2$OCH$_3$ | H | COC$_6$H$_5$ |
| OH | OH | CH$_3$ | CH$_3$ | H | COCH$_3$ |
| OH | OH | H | CH$_3$ | H | COCH$_3$ |
| OH | OH | C$_2$H$_5$ | C$_2$H$_5$ | H | COCH$_3$ |
| OH | OH | H | C$_2$H$_5$ | H | COCH$_3$ |
| OH | OH | H | CH$_2$OH | H | COCH$_3$ |
| OH | OH | CH$_2$NH$_2$ | CH$_2$NH$_2$ | H | COCH$_3$ |
| OH | OH | CH$_2$OH | CH$_2$OH | H | COCH$_3$ |
| OH | OH | CH$_2$Cl | CH$_2$Cl | H | COCH$_3$ |
| OH | OH | CH$_3$ | CH$_2$OCOCH$_3$ | H | CH$_3$ |
| SH | OH | CH$_3$ | CH$_3$ | H | COCH$_3$ |
| SH | SH | H | CH$_2$OH | H | COCH$_3$ |

TABLE IV

| B | B$_1$ | R'$_1$ | R'$_2$ | R'$_3$ | R'$_4$ |
|---|---|---|---|---|---|
| OH | OH | CH$_3$ | CH$_2$OCH$_3$ | H | COC$_6$H$_5$ |
| OH | OH | CH$_3$ | CH$_3$ | H | COCH$_3$ |
| OH | OH | H | CH$_3$ | H | COCH$_3$ |
| OH | OH | C$_2$H$_5$ | C$_2$H$_5$ | H | COCH$_3$ |
| OH | OH | H | C$_2$H$_5$ | H | COCH$_3$ |
| OH | OH | H | CH$_2$OH | H | COCH$_3$ |
| OH | OH | CH$_2$NH$_2$ | CH$_2$NH$_2$ | H | COCH$_3$ |
| OH | OH | CH$_2$OH | CH$_2$OH | H | COCH$_3$ |

TABLE IV-continued

| B | B$_1$ | R'$_1$ | R'$_2$ | R'$_3$ | R'$_4$ |
|---|---|---|---|---|---|
| OH | OH | CH$_2$Cl | CH$_2$Cl | H | COCH$_3$ |
| OH | OH | CH$_3$ | CH$_2$OCOCH$_3$ | H | CH$_3$ |
| SH | OH | CH$_3$ | CH$_3$ | H | COCH$_3$ |
| SH | SH | H | CH$_2$OH | H | COCH$_3$ |

EXAMPLE 6

N,N'-dicarbobenzyloxy-6'-hydroxy-spectinomycin

N,N-dicarbobenzyloxy-6'-acetoxyspectinomycin (0.4 g) is added to a slurry of dipotassium hydrogen phosphate (0.40 g) in anhydrous methanol (20 ml) and stirred at room temperature for 1½ hours. The solvent is removed at reduced pressure and the organics dissolved in 1½ percent methanol in chloroform and chromatographed on silica gel (225 g) using 1½ percent methanol in chloroform. The product containing fractions are combined and concentrated to yield N,N'-dicarbobenzyloxy-6'-hydroxyspectinomycin.

Utilizing procedures similar to those of Example 6, but substituting the appropriately substituted N,N'-dicarbobenzyloxy-6'-hydroxy-spectinomycin for N,N'-dicarbobenzyloxy-6'-acetoxyspectinomycin there is obtained the protected analogs of Tables V and VI

TABLE V

| B | B$_1$ | R'$_1$ | R'$_2$ | R'$_3$ |
|---|---|---|---|---|
| HO— | HO— | H—' | HOCH$_2$— | H |
| CH$_3$O— | HO— | — | — | — |
| C$_2$H$_5$O— | HO— | — | — | — |
| HS— | HO— | — | — | — |
| CH$_3$S— | HO— | — | — | — |
| C$_2$H$_5$S— | HO— | — | — | — |
| H— | HO— | — | — | — |
| HO— | H— | — | — | — |
| HO— | CH$_3$O— | — | — | — |
| HO— | C$_2$H$_5$— | — | — | — |
| HO— | HS— | — | — | — |
| HO— | CH$_3$S— | — | — | — |
| HO— | C$_2$H$_5$S— | — | — | — |
| HO— | — | — | HOCH$_2$— | CH$_2$OCH$_2$ |
| HO— | — | — | — | C$_2$H$_5$ |

TABLE VI

| B | B₁ | R'₁ | R'₂ | R'₃ |
|---|----|-----|-----|-----|
| HO— | HO— | H— | HOCH₂— | H |
| CH₃O— | HO— | — | — | — |
| C₂H₅O— | HO— | — | — | — |
| HS— | HO— | — | — | — |
| CH₃S— | HO— | — | — | — |
| C₂H₅S— | HO— | — | — | — |
| H— | HO— | — | — | — |
| HO— | H— | — | — | — |
| HO— | CH₃O— | — | — | — |
| HO— | C₂H₅— | — | — | — |
| HO— | HS— | — | — | — |
| HO— | CH₃S— | — | — | — |
| HO— | C₂H₅S— | — | — | — |
| HO— | — | — | HOCH₂— | CH₂OCH₂C₂H₅ |
| HO— | — | — | — | C₂H₅ |

EXAMPLE 7

N,N'-biscarbobenzyloxy-2'-O-benzoyl-4',5'-didehydrospectinomcyin

A chromatographed mixture of the anomers prepared in Example 3 (0.51 g) is dissolved in acetonitrile (6.0 ml) and potassium carbonate (0.35 g) is added and stirred with protection from atmospheric moisture. After 46 hours the solid is filtered off, washed with acetonitrile and the filtrate is concentrated. The residue is chromatographed on 75 ml of silica gel which is wet packed in 1:9 acetone-chloroform. Fractions of 20 ml volume are taken. After the 19th fraction, the major product ($R_f$=0.23 in 1:9 acetone-chloroform) is eluted. The product containing fractions are combined and concentrated to 0.15 g of N,N'-bis-carbobenzoyloxy-2-O-benzoyl-4',5'-didehydrospectinomycin.

MS(disilyl): 846 (M+), 831 (M−15), 724, 680, 589. High resolution, 846.3233 found:

$C_{43}H_{54}N_2O_{12}S_2$ requires 846.3215.

CD (CH₃OH): $[\theta]_{311}^{max} = -20,000 \pm 1,200$; $[\theta]_{241}^{max} = +19,400 \pm 1,200$.

UV in CH₃CN: $\lambda_{max}$ 267 ($\epsilon$=12,600), 232 ($\epsilon$=17,100).

PMR (CDCL₃): 2.10 (S, 3H), 2.80 (S, 3H), 2.88 (S, 3H), 5.18 (S, 4H), 5.50 (S, 1H), 6.25 (S, 1H), 7.15–7.70 (M, 13H), 7.90–8.10δ (M, 2H).

CMR in CD₃COCD₃: 20.1, 31.7, 57.2, 57.3, 60.1, 60.7, 66.1, 67.4, 68.0, 74.6, 74.8, 75.6, 80.5, 94.6, 96.3, 103.4, 128.3, 129.2, 129.6, 130.1, 130.4, 130.6, 134.7, 139.5, 158.4, 168.0, 173.8, 184.4 ppm.

EXAMPLE 8

N,N'-biscarbobenzyloxy-2-O-acetyl-4',5'-didehydrospectinomycin

A chromatographed mixture of the anomers prepared in Example 2 is dissolved in acetonitrile (6.0 ml) and potassium carbonate (0.35 g) is added and stirred with protection from atmospheric moisture. After 46 hours the solid is filtered off, washed with acetonitrile and the filtrate is concentrated. The residue is chromatographed on 75 ml of silica gel which is wet packed in 1:9 acetone chloroform. Fractions of 20 ml volumn are taken and the major product is eluted. The product containing fractions are combined and concentrated to give N,N'-bis-carbobenzyloxy-2-O-acetyl-4',5'-didehydro-spectinomycin.

Using a procedure similar to that outlined in Examples 7 and 8, but substituting the appropriately substituted mixture of anomers for the mixture used therein there is obtained the protected didehydrospectinomycin analogs of Tables VII and VIII.

TABLE VII

| B | B₁ | R'₁ | R'₃ | R₁₅ |
|---|-----|-----|-----|-----|
| HO— | HO— | H | H | CH₃C(O)— |
| CH₃O— | HO— | H | H | CH₃C(O)— |
| C₂H₅O— | HO— | H | H | CH₃C(O)— |
| HS— | HO— | H | H | CH₃C(O)— |
| CH₃S— | HO— | H | H | CH₃C(O)— |
| C₂H₅S— | HO— | H | H | CH₃C(O)— |
| H— | HO— | H | H | CH₃C(O)— |
| HO— | H— | H | H | CH₃C(O)— |
| HO— | CH₃O— | H | H | CH₃C(O)— |
| HO— | C₂H₅— | H | H | CH₃C(O)— |
| HO— | H₂— | H | H | CH₃C(O)— |
| HO— | CH₃S— | H | H | CH₃C(O)— |
| HO— | C₂H₅S— | H | H | CH₃CH₂C(O)— |
| HO— | HO— | H | H | CH₃CH₂C(O)— |
| HO— | HO— | CH₃O—CH(CH₃)— | H | CH₃(CH₂)₂C(O)— |

TABLE VII-continued

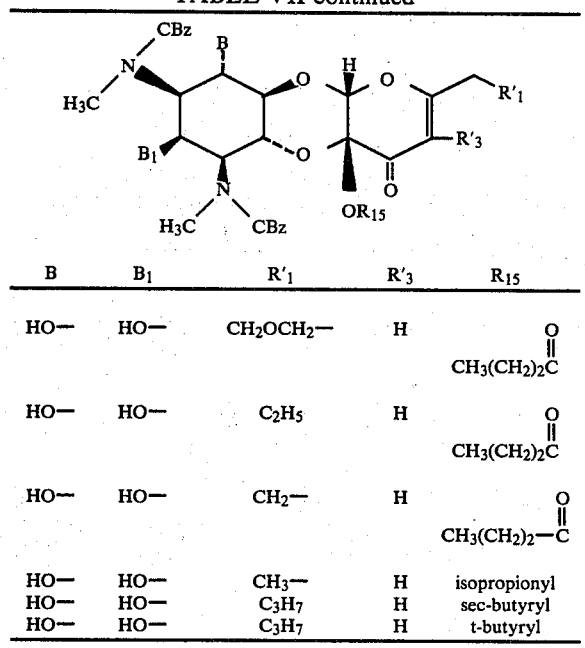

| B | $B_1$ | $R'_1$ | $R'_3$ | $R_{15}$ |
|---|---|---|---|---|
| HO— | HO— | $CH_2OCH_2$— | H | $CH_3(CH_2)_2\overset{O}{\underset{\|}{C}}$ |
| HO— | HO— | $C_2H_5$ | H | $CH_3(CH_2)_2\overset{O}{\underset{\|}{C}}$ |
| HO— | HO— | $CH_2$— | H | $CH_3(CH_2)_2\overset{O}{\underset{\|}{C}}$ |
| HO— | HO— | $CH_3$— | H | isopropionyl |
| HO— | HO— | $C_3H_7$ | H | sec-butyryl |
| HO— | HO— | $C_3H_7$ | H | t-butyryl |

TABLE VIII

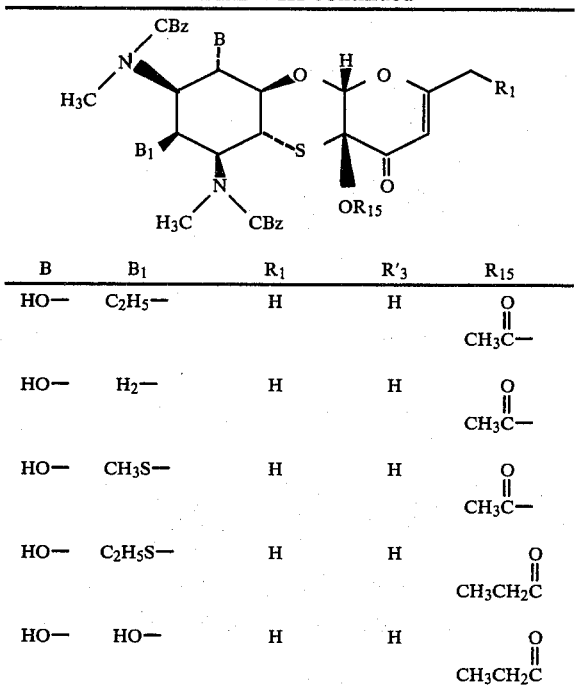

| B | $B_1$ | $R_1$ | $R'_3$ | $R_{15}$ |
|---|---|---|---|---|
| HO— | HO— | H | H | $CH_3\overset{O}{\underset{\|}{C}}$— |
| $CH_3O$— | HO— | H | H | $CH_3\overset{O}{\underset{\|}{C}}$— |
| $C_2H_5O$— | HO— | H | H | $CH_3\overset{O}{\underset{\|}{C}}$— |
| HS— | HO— | H | H | $CH_3\overset{O}{\underset{\|}{C}}$— |
| $CH_3S$— | HO— | H | H | $CH_3\overset{O}{\underset{\|}{C}}$— |
| $C_2H_5S$— | HO— | H | H | $CH_3\overset{O}{\underset{\|}{C}}$— |
| H— | HO— | H | H | $CH_3\overset{O}{\underset{\|}{C}}$— |
| HO— | H— | H | H | $CH_3\overset{O}{\underset{\|}{C}}$— |
| HO— | $CH_3O$— | H | H | $CH_3\overset{O}{\underset{\|}{C}}$— |

TABLE VIII-continued

| B | $B_1$ | $R_1$ | $R'_3$ | $R_{15}$ |
|---|---|---|---|---|
| HO— | $C_2H_5$— | H | H | $CH_3\overset{O}{\underset{\|}{C}}$— |
| HO— | $H_2$— | H | H | $CH_3\overset{O}{\underset{\|}{C}}$— |
| HO— | $CH_3S$— | H | H | $CH_3\overset{O}{\underset{\|}{C}}$— |
| HO— | $C_2H_5S$— | H | H | $CH_3CH_2\overset{O}{\underset{\|}{C}}$ |
| HO— | HO— | H | H | $CH_3CH_2\overset{O}{\underset{\|}{C}}$ |
| HO— | HO— | $CH_2O—CH(CH_3)$— | H | $CH_3(CH_2)_2\overset{O}{\underset{\|}{C}}$ |
| HO— | HO— | $CH_2OCH_2$— | H | $CH_3(CH_2)_2\overset{O}{\underset{\|}{C}}$ |
| HO— | HO— | $C_2H_5$— | H | $CH_3(CH_2)_2\overset{O}{\underset{\|}{C}}$ |
| HO— | HO— | $CH_2$— | H | $CH_3(CH_2)_2$—$\overset{O}{\underset{\|}{C}}$ |
| HO— | HO— | $CH_3$ | H | isopropionyl |
| HO— | HO— | $C_2H_7$ | H | sec-butyryl |
| HO— | HO— | $C_2H_7$ | H | t-butyryl |

EXAMPLE 9

N,N'-biscarbobenzyloxy-4',5'-didehydrospectinomycin

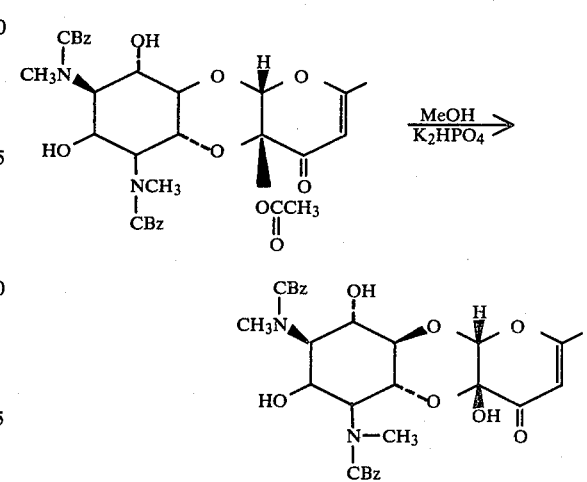

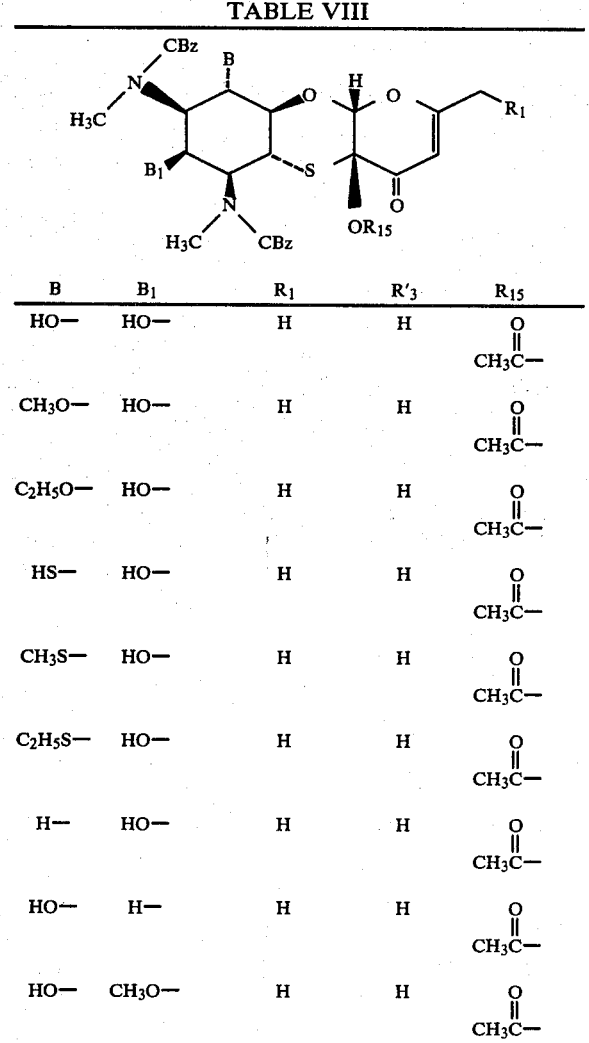

N,N'-biscarbobenzyloxy-2'-O-acetyl-4',5'-didehydrospectinomycin (1.0 g) is added to a slurry of dipotassium hydrogen phosphate (0.40 g) in anhydrous methanol (20 ml) and stirred at room temperature for 1½ hours. The solvent is removed at reduced pressure and the organics dissolved in 1½ percent methanol in chloroform and chromatographed on silica gel (225 g) using 1½ percent methanol in chloroform. The product containing fractions are combined and concentrated to yield 0.51 g (55 percent) of N,N'-biscarbobenzyloxy-4',5'-didehydrospectinomycin.

CD (CH$_3$OH): $[\theta]_{314}^{max}$ $-8,300\pm2,100$, $[\theta]_{266}^{max}$ $+10,500$ $2,100$ $[\alpha]_D$ $-56°$ (C 1.0, CH$_3$OH)

CMR (CD$_3$COCD$_3$): 187.6, 175.8, 157.2, 138.1, 128.4, 101.7, 99.3, 87.7, 76.3, 64.6, 63.8, 67.3, 66.7, 66.3, 65.3, 60.8, 60.0, 31.5, 21.3 ppm.

Mass spectrum: m/e (triTMS): 814 (M+), 799 (M−15).

EXAMPLE 10

N,N'-biscarbobenzyloxy-4',5'-didehydrospectinomycin

N,N'-biscarbobenzyloxy-2'-O-benzoyl-4,5'-didehydrospectinomycin (0.13) is dissolved in methanol and potassium sodium tartarate tetrahydrate (120 mg) is stirred in at room temperature. After about 5 days at room temperature and 8 hours at 50° the solid is filtered off and the filtrate concentrated. The crude material is taken up in 2% methanol in chloroform and chromatographed on silica gel (50 ml). By pooling appropriate fractions starting materials (34 mg) is recovered as well as enone product (19 mg). The material made in this way is identical by CMR to a reference (see U.S. application Ser. No. 020,073, filed Mar. 13, 1979).

Utilizing a procedure similar to that used in Examples 9 and 10 but substituting the appropriately substituted didehydrospectinomycin derivative for N,N'-bis-carbobenzyloxy-2'-O-acetyl-4',5'-didehydrospectinomycin there is obtained the protected didehydrospectinomycin analogs of Tables IX and X.

TABLE IX

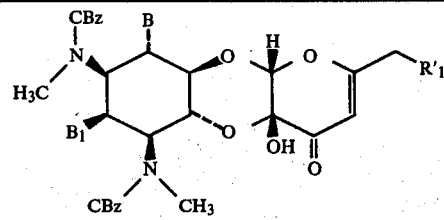

| B | B$_1$ | R'$_1$ |
|---|---|---|
| HO— | HO— | H |
| CH$_3$O— | HO— | H |
| C$_2$H$_5$O— | HO— | H |
| HS— | HO— | H |
| CH$_3$S— | HO— | H |
| C$_2$H$_5$S— | HO— | H |
| H— | HO— | H |
| HO— | H— | H |
| HO— | CH$_2$O— | H |
| HO— | C$_2$H$_5$— | H |
| HO— | H$_2$— | H |
| HO— | CH$_3$S— | H |
| HO— | C$_2$H$_5$S— | H |
| HO— | HO— | H |
| HO— | HO— | H |
| HO— | HO— | CH$_3$OCH$_2$— |
| HO— | HO— | C$_2$H$_2$ |
| HO— | HO— | CH$_3$— |
| HO— | HO— | CH$_3$— |

TABLE IX-continued

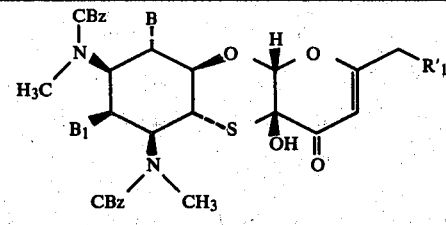

| B | B$_1$ | R'$_1$ |
|---|---|---|
| HO— | HO— | C$_2$H$_7$ |

TABLE X

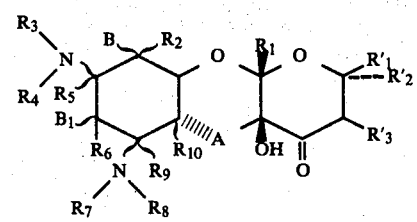

| B | B$_1$ | R'$_1$ |
|---|---|---|
| HO— | HO— | H |
| CH$_3$O— | HO— | H |
| C$_2$H$_5$O— | HO— | H |
| HS— | HO— | H |
| CH$_2$S— | HO— | H |
| C$_2$H$_5$S— | HO— | H |
| H— | HO— | H |
| HO— | H— | H |
| HO— | CH$_2$O— | H |
| HO— | C$_2$H$_5$— | H |
| HO— | H$_2$— | H |
| HO— | CH$_2$S— | H |
| HO— | C$_2$H$_5$S— | H |
| HO— | HO— | H |
| HO— | HO— | H |
| HO— | HO— | CH$_3$OCH$_2$— |
| HO— | HO— | C$_2$H$_5$ |
| HO— | HO— | CH$_3$ |
| HO— | HO— | CH$_3$ |
| HO— | HO— | C$_2$H$_7$ |

I claim:

1. A process for preparing anomers and asteric mixtures of a compound having the formula:

Ia

[Structure with R$_1$, R$_2$, R$_3$, R$_4$, R$_5$, R$_6$, R$_7$, R$_8$, R$_9$, R$_{10}$, B, B$_1$, A, R'$_1$, R'$_2$, R'$_3$]

which comprises
(a) reacting a compound having the formula:

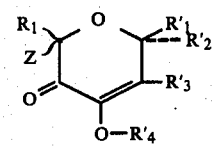

with a compound having the formula

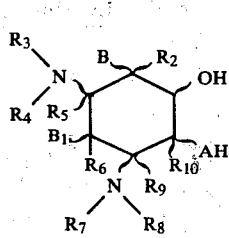

to prepare a compound having the formula

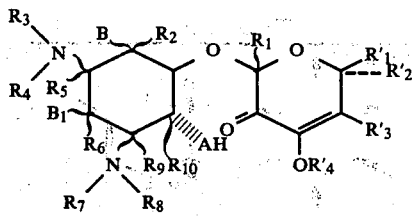

IVa (b) reacting the compound prepared in Step (a) with silica gel to prepare a compound having the formula

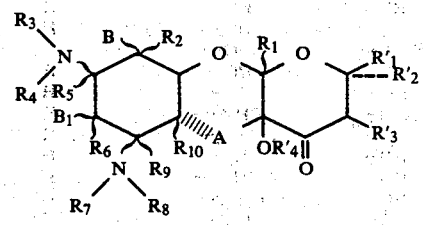

(c) subjecting the compound prepared in Step (b) to alcoholysis to form a compound having the formula

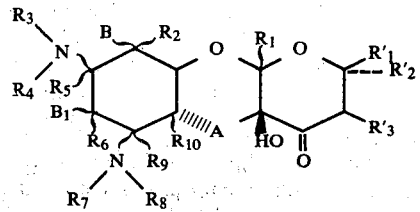

and (d) hydrolyzing the compound prepared in Step (c) to prepare the compound of Formula Ia;

Wherein $R'_1$ through $R'_3$ are the same or different and are selected from the group consisting of hydrogen, lower alkyl, acyloxyalkyl, lower haloalkyl, lower aminoalkyl, lower alkenyl, lower alkynyl, —OX and —(CH$_2$)n-OX and isomers thereof; with the proviso that $R'_1$ $R'_2$ and $R'_3$ are not hydroxy;

X is selected from the group consisting of hydrogen, lower alkyl, lower alkenyl, and lower alkynyl;

n is an integer of from one to four;

$R_1$ is hydrogen or lower alkyl;

wherein $R_2$, $R_5$, $R_6$, $R_9$ and $R_{10}$ are selected from the group consisting of hydrogen, lower alkyl, lower alkenyl and lower alkynyl; $R_3$, $R_4$, $R_7$ and $R_8$ are selected from the group consisting of hydrogen, lower alkyl, lower alkenyl, lower alkynyl, and a blocking group selected from the group consisting of aralkoxycarbonyl, halogenated alkoxycarbonyl and alkoxycarbonyl; with the proviso that one of $R_3$ and $R_4$ is always a blocking group and one of $R_7$ and $R_8$ is always a blocking group; $R'_4$ is aroyl lower alkyl or acyl; A is selected from the group consisting of oxygen and sulfur; B and $B_1$ are the same or different and are selected from the group consisting of hydrogen, hydroxy, alkoxy, o-lower alkenyl, thio, thio-lower alkyl and thio-lower alkenyl and Z is halo.

* * * * *